(12) United States Patent
Weyl et al.

(10) Patent No.: US 7,254,984 B2
(45) Date of Patent: Aug. 14, 2007

(54) SENSOR

(75) Inventors: Helmut Weyl, Wiesbaden (DE); Frank Meier, Kornwestheim (DE); Peter Dettling, Waiblingen (DE); Bettina Schneider, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 29 days.

(21) Appl. No.: 10/512,741

(22) PCT Filed: May 14, 2003

(86) PCT No.: PCT/DE03/01549

§ 371 (c)(1),
(2), (4) Date: May 6, 2005

(87) PCT Pub. No.: WO03/098203

PCT Pub. Date: Nov. 27, 2003

(65) Prior Publication Data

US 2005/0201900 A1    Sep. 15, 2005

(30) Foreign Application Priority Data

May 17, 2002   (DE) ................................ 102 22 567
Dec. 23, 2002  (DE) ................................ 102 60 842

(51) Int. Cl.
*G01N 27/403* (2006.01)

(52) U.S. Cl. .............. 73/23.31; 73/23.2; 73/31.05; 422/88; 422/94; 422/98; 204/424; 204/428

(58) Field of Classification Search ............. 73/23.2, 73/23.31, 31.05; 422/88, 94, 98; 204/424, 204/426, 428, 431
See application file for complete search history.

(56) References Cited

U.S. PATENT DOCUMENTS

| 4,236,138 A | * | 11/1980 | Segawa et al. ............. 338/34 |
| 4,277,439 A |   | 7/1981  | Yasuda et al. ............. 422/94 |
| 4,453,397 A | * | 6/1984  | Ohta et al. ............... 73/23.31 |
| 4,597,850 A | * | 7/1986  | Takahasi et al. .......... 204/426 |
| 5,144,249 A |   | 9/1992  | Kurishita et al. |
| 5,246,562 A | * | 9/1993  | Weyl et al. ............... 204/424 |

FOREIGN PATENT DOCUMENTS

| DE | 41 26 378  | 4/1992 |
| DE | 195 42 650 | 5/1997 |
| DE | 197 06 208 | 8/1998 |
| DE | 199 41 051 | 3/2001 |
| DE | 101 15 704 | 9/2002 |
| EP | 1 037 039  | 9/2000 |

\* cited by examiner

*Primary Examiner*—Daniel S. Larkin
(74) *Attorney, Agent, or Firm*—Kenyon & Kenyon LLP

(57) ABSTRACT

A sensor for measuring a physical property of a measuring gas, in particular the oxygen concentration or the temperature in the exhaust gas of an internal combustion engine in a motor vehicle, has a housing, a measuring element whose end section protrudes from the housing, a connector plug mounted on the end section, and a housing shell covering the end section and connector plug with a radial clearance, one shell end of the housing shell being attached to the housing and the other shell end being sealed. To prevent electromechanical breakage in the sensor in the event of extreme vibration stresses or accelerations of the vehicle, the free space within the housing shell is completely filled with a non-conductive granulate.

11 Claims, 2 Drawing Sheets

SENSOR

FIELD OF THE INVENTION

The present invention relates to a sensor for measuring a physical property of a measuring gas, in particular the oxygen concentration or the temperature in the exhaust gas of an internal combustion engine in a motor vehicle.

BACKGROUND INFORMATION

Such a sensor is described in, for example, German Patent No. DE 41 26 378 and German Patent Application No. DE 195 42 650. A measuring element having a planar stratified design such as described in German Patent Application No. DE 199 41 051, for example, has electrically conductive contact surfaces on its end section protruding from the housing on the connection side, which are contacted by the connector plug. The connector plug has two contact part supports which are pressed onto opposite sides of the measuring element's end section, a contact part of each support resting on the contact surfaces. To ensure proper electrical contact, the two contact part supports are pressed onto the end section of the measuring element using a friction spring which encloses both contact part supports on the outside. The contact parts made of strip-shaped sheets of metal extend beyond the contact part support and form connecting points of connecting cables, each contact part being crimped with one connecting cable. The crimped points are within a molded body which occludes the housing shell, and the connecting cables pass through this molded body.

SUMMARY

An example sensor according to the present invention may advantageously have a high degree of robustness which prevents the sensor from sustaining mechanical or electrical damage even under extreme conditions of use of the vehicle, such as high-speed or off-road operation. By filling the free space around the connector plug in accordance with the present invention with a material, even extreme vibration stresses and vibration accelerations at the connector plug are appropriately damped and thus breakage in the area of the electromechanical contact, e.g., of the contact parts, contact support, and/or the friction spring is avoided.

According to a preferred embodiment of the present invention, the material is filled in as a bulk material, whereby the free space within the housing shell is completely filled in a considerably easier manner.

According to a preferred embodiment of the present invention, quartz sand or granulated corundum or granulated plastic is used. The finer the grains of the granulate, the better the entire available space is filled and the better the damping effect in the case of vibration stresses.

According to a preferred embodiment of the present invention, the material is a temperature-resistant, porous foam. Such a foam has the advantage that it is not so hard as to cause stresses in the component, which might result in breakage of the measuring element. Its hardness may be adjusted via the amount of the foam-forming material filled into the free space. In contrast with ceramic cast compounds, the foam has sufficient permeability for oxygen, so that such a sensor may be used as a maximum current probe with pumped reference in particular.

According to an advantageous embodiment of the present invention, orthosilicic acid ($H_4SiO_4$) is used as the foam-building material, the molecules of which assume a colloidal structure when water is split off and silicon dioxide chain molecules are formed. By heating to temperatures over 100° C., the water still present is evaporated, thereby swelling the foam. A foam of silicon dioxide ($SiO_2$) remains, whose degree of dryness, i.e., moisture content of the colloidal solution, may influence its porosity. A lower residual moisture results in low porosity and correspondingly greater firmness of the foam.

According to an advantageous embodiment of the present invention, the housing shell end facing away from the housing is occluded by a molded body, and a radial borehole is situated in the housing shell above the connector plug and another borehole is situated below the connector plug. The lower borehole is used for introducing the foam-forming material into the housing, the pore size and the firmness of the resulting foam also being influenceable by the size of the borehole. After the foam-forming material has been filled in, the lower borehole is sealed, for example via welding. The upper borehole is used for removing the evaporating water during the heating process and for visually checking that the free space is completely filled with foam.

BRIEF DESCRIPTION OF THE DRAWINGS

The present invention is explained in greater detail in the subsequent description with reference to an exemplary embodiment illustrated in the figures.

DETAILED DESCRIPTION OF EXAMPLE EMBODIMENTS

Figure 1:
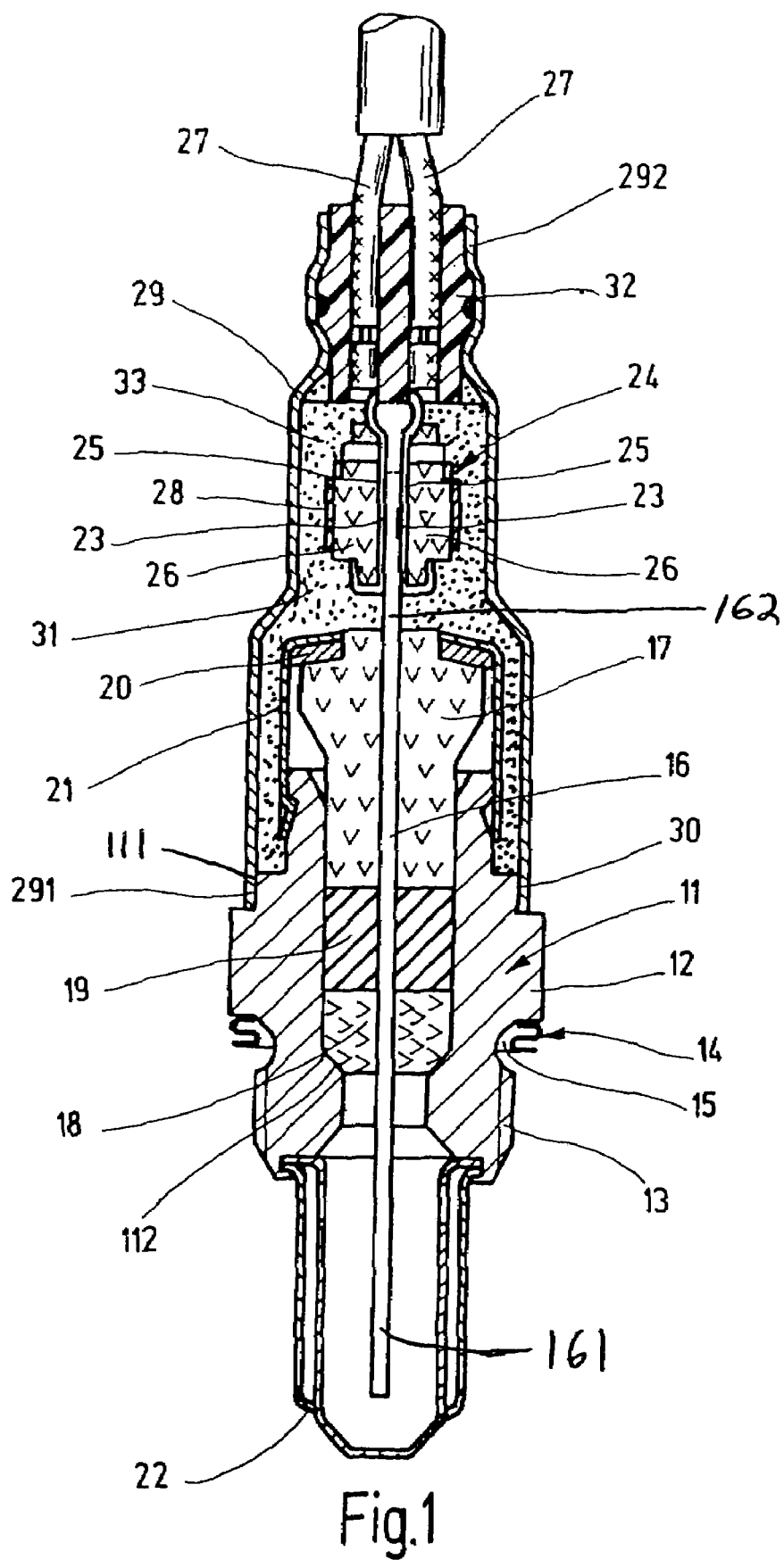
FIG. 1 shows a longitudinal section of a sensor for measuring the oxygen concentration in the exhaust gas of an internal combustion engine.

An example sensor for measuring the oxygen concentration in the exhaust gas of an internal combustion engine in a motor vehicle illustrated in FIG. 1 as a longitudinal section, also known as a lambda probe, as an exemplary embodiment for a generic sensor for measuring a physical property of a measuring gas, has a metallic housing 11, which has a hexagon 12 and a thread 13 on the outside for the installation of the sensor in an exhaust gas fitting of the multi-cylinder internal combustion engine. A sealing ring 14, which is firmly secured in an annular groove 15 in housing 11, is used for the hermetic installation of the sensor in the exhaust gas fitting.

An electrochemical measuring element 16, whose design is described in German Patent Application No. DE 199 41 051, for example, is accommodated in housing 11. It is pressed radially into the center of housing 11 via a packet of two electrically insulating ceramic parts 17, 18 having a seal 19 between them and is axially fixed in housing 11, its end section on the measuring gas side 161 and on its end section on the connection side 162 protruding from housing 11. A support shoulder 112 in housing 11, a compression spring 20, which rests on a ceramic part 17, and a cover 21, which spans spring 20 and whose edge is engaged in housing 11, are used for axially fixing the measuring element. Gas-sensitive end section 161 of measuring element 16 is covered by a double protective tube 22, which is secured to housing 11.

There are contact surfaces 23, via which measuring element 16 is contacted, on sides facing away from one another on connection side end section 162 of measuring element 16, which passes through the center of cover 21. Used for this purpose is connector plug 24, which carries a number of contact parts 25 corresponding to the number of contact surfaces 23, the contact parts being supported on two ceramic contact part supports 26. Contact parts 25 designed as strip-shaped sheets of metal extend beyond contact part support 26, and each end is crimped with a connecting cable 27. Contact part support 16 situated opposite connection side end section 162 is enclosed on the outside by a friction spring 28, whereby a sufficiently high contact pressure is produced between contact parts 25 and contact surfaces 23.

A housing shell 29 is pushed over connection side end section 162 of measuring element 16, which carries connector plug 24, one shell end 291 of this housing shell enclosing a collar 111 formed externally on housing 11 and is fixed there in a gas-tight manner, for example, by a circumferential weld 30. Housing shell 29 surrounds connector plug 24 and cover 21 with a radial gap, in such a way that a free space 31 is formed inside housing shell 29. This free space 31 is bordered by cover 21 and by a plastic molded body 32, which is pushed into shell end 292 of housing shell 29 facing away from housing 11 and pressed onto it. Connecting cables 27 are then passed through molded body 32 in such a way that the crimped connections between contact parts 25 and connecting cables 27 are still within molded body 22.

To make the thus constructed sensor insensitive to vibration stresses and vibration accelerations, free space 31 is filled with a material 33, which is introduced as a bulk material into free space 31 prior to installation of molded body 32 in housing shell 29. A non-conductive, inorganic material in granulate form is used as material 33, for example quartz sand, granulated corundum, or a granulated plastic. Free space 31 filled with material has a strong damping effect on measuring element 16, which prevents breakage from occurring in the area of the electromechanical contacts, e.g., of contact part support 26, contact parts 25, or friction springs 28, even in the event of extreme vibration stresses or extreme accelerations of the motor vehicle.

Figure 2:
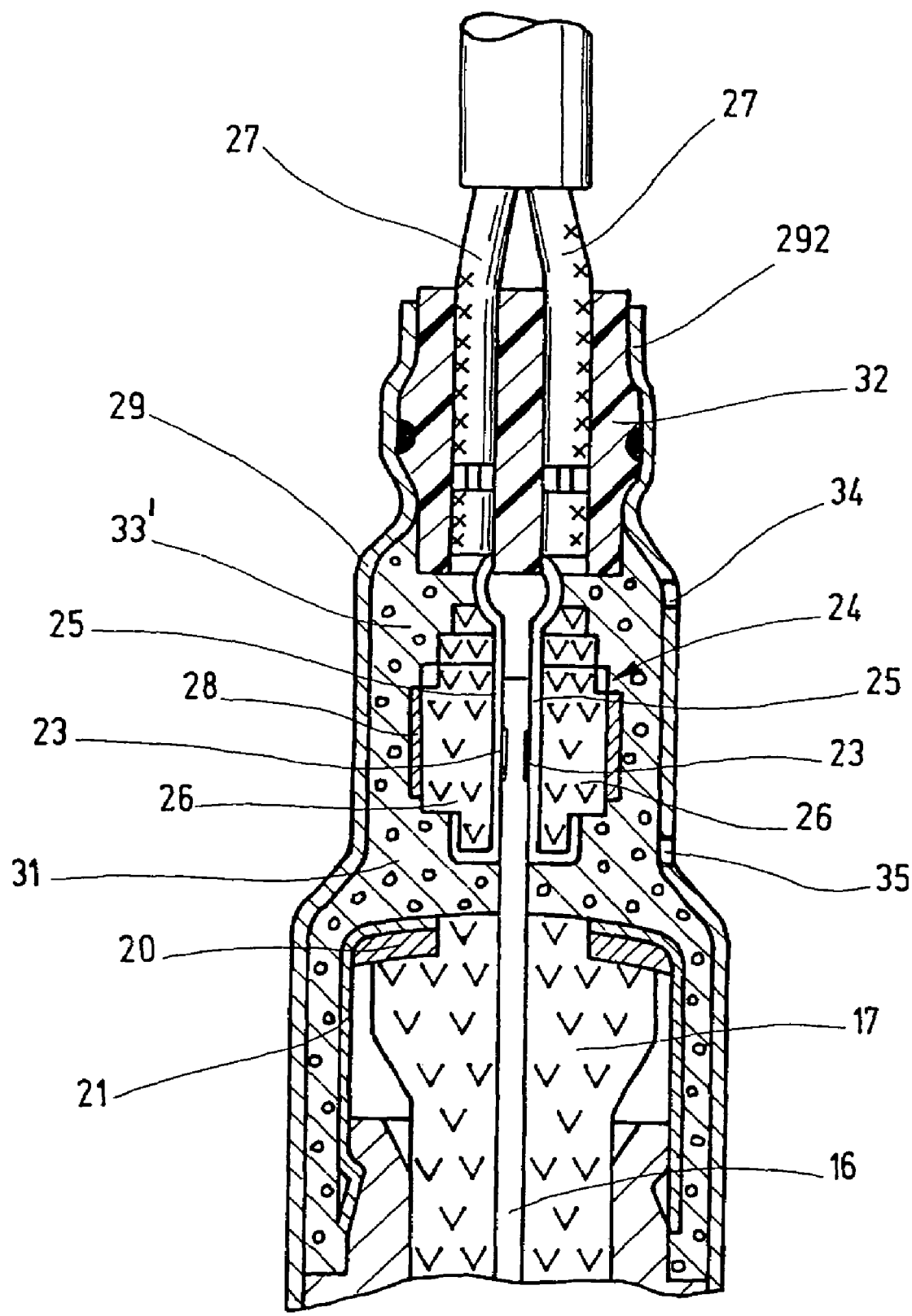
FIG. 2 shows a section of the same illustration as FIG. 1, including a modification of the sensor.

The sensor illustrated in FIG. 2 as an enlarged section is modified with respect to the sensor described in connection with FIG. 1 in that material 33' filled into free space 31 within housing shell 29 is a foam, whose porosity, i.e. firmness, is suitably adjusted. Orthosilicic acid ($H_4SiO_4$) is advantageously used as a foam-forming material, whose molecules assume a colloidal structure given the splitting off of water and the forming of

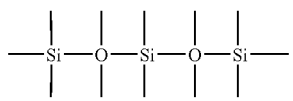

chain molecules.

Two boreholes 34 and 35 are made in housing shell 29, upper borehole 34 preferably being situated above connector plug 24 and lower borehole 35 being situated below connector plug 24. The foam-forming material is introduced via lower radial borehole 35, and lower borehole 35 is subsequently sealed. The water ($H_2O$) contained in the orthosilicic acid is evaporated by heating the sensor to a temperature above 100° C. and swelling the foam being formed. The evaporating water exits via upper borehole 34. After completion of the heating process, free space 31 is fully filled with a foam 33' made of silicon dioxide ($SiO_2$), whose porosity is influenceable by its degree of dryness. A higher firmness of foam 33' requires a lower residual moisture. In addition to influencing the foam by the residual moisture, the pore size and thus the firmness of the foam may also be influenced by the amount of the colloidal solution filled into free space 31 as well as the clear cross section of lower borehole 35. Borehole 35 preferably has a diameter between 1 mm and 3 mm.

The present invention is not limited to the described sensor for measuring oxygen concentration in the exhaust gas of internal combustion engines. Thus, in sensors for measuring the concentration of nitrogen oxides in the exhaust gas or in sensors for measuring the temperature of the exhaust gas, the same advantageous effects are achievable by introducing material 33 or 33' into free space 31 within housing shell 29.

What is claimed is:

1. A sensor for measuring a physical property of an oxygen concentration or a temperature in an exhaust gas of an internal combustion engine in a motor vehicle, comprising:
   a housing;
   a measuring element accommodated in the housing, the measuring element having an end section that protrudes from the housing;
   a connector plug mounted on the end section; and
   a housing shell which covers the end section and the connector plug with a radial clearance, the housing shell having a first shell end that is attached to the housing, and a second shell end that is sealed;
   wherein a free space present inside the housing shell is completely filled with a material;
   wherein the material is filled in as a bulk material;
   wherein the material is a non-conductive, inorganic material in the form of a granulate; and
   wherein the material is one of quartz sand or granulated corundum.

2. The sensor as recited in claim 1, wherein after the material is filled in, a molded body is introduced into the housing shell to seal the second shell end of the housing shell facing away from the housing, connecting cables connected to the connector plug being passed through the molded body.

3. The sensor as recited in claim 2, wherein the housing shell and the molded body are radially pressed together.

4. The sensor as recited in claim 1, wherein the housing shell is attached in a gas-tight manner to the housing.

5. The sensor as recited in claim 4, wherein a shell edge of the housing shell is welded to the housing.

6. A sensor for measuring a physical property of an oxygen concentration or a temperature in an exhaust gas of an internal combustion engine in a motor vehicle, comprising:
   a housing;
   a measuring element accommodated in the housing, the measuring element having an end section that protrudes from the housing;
   a connector plug mounted on the end section; and
   a housing shell which covers the end section and the connector plug with a radial clearance, the housing shell having a first shell end that is attached to the housing, and a second shell end that is sealed;
   wherein a free space present inside the housing shell is completely filled with a material; and
   wherein the material is a temperature-resistant, porous foam.

7. The sensor as recited in claim 6, wherein orthosilicic acid ($H_4SiO_4$) is used as a foam-forming material, the molecules of which assume a colloidal structure when water is split off and silicon dioxide chain molecules are formed.

8. The sensor as recited in claim 7, wherein the second shell end of the housing shell facing away from the housing is occluded by a molded body, through which connecting cables connected to the connector plug are passed, and an upper radial borehole, which is situated above the connector plug, and a lower radial borehole, which is situated below the connector plug and is used for introducing the foam-forming material, are positioned in the housing shell.

9. The sensor as recited in claim 8, wherein the lower borehole is sealed, after the introduction of the foam-forming material.

10. The sensor as recited in claim 9, wherein the lower borehole is welded shut.

11. The sensor as recited in claim 8, wherein a diameter of the lower borehole is approximately 1 mm to 3 mm.

* * * * *